(12) United States Patent
Terfort et al.

(10) Patent No.: US 10,794,908 B2
(45) Date of Patent: Oct. 6, 2020

(54) FUNCTIONALIZED NANOMEMBRANE, A METHOD FOR PREPARATION THEREOF AND THEIR USE

(71) Applicants: Johann Wolfgang Goethe-Universität, Frankfurt am Main (DE); Max-Planck-Gesellschaft zur Förderung der Wissenschaften e.V., Munich (DE)

(72) Inventors: Andreas Terfort, Halstenbek (DE); Daniel Rhinow, Frankfurt am Main (DE); Andrey Turchanin, Jena (DE)

(73) Assignees: Max-Planck-Gesellschaft zur Förderung der Wissenschaften e.V., Munich (DE); Quantifoil Micro Tools GmbH, Großlöbichau/Jena (DE)

( * ) Notice: Subject to any disclaimer, the term of this patent is extended or adjusted under 35 U.S.C. 154(b) by 92 days.

(21) Appl. No.: 15/546,736

(22) PCT Filed: Jan. 29, 2016

(86) PCT No.: PCT/EP2016/051923
§ 371 (c)(1),
(2) Date: Jul. 27, 2017

(87) PCT Pub. No.: WO2016/120450
PCT Pub. Date: Aug. 4, 2016

(65) Prior Publication Data
US 2018/0017558 A1  Jan. 18, 2018

(30) Foreign Application Priority Data

Jan. 29, 2015  (EP) .................................... 15153106

(51) Int. Cl.
*G01N 33/569* (2006.01)
*H01J 37/20* (2006.01)
(Continued)

(52) U.S. Cl.
CPC .. *G01N 33/56911* (2013.01); *B01J 20/28033* (2013.01); *B01J 20/3242* (2013.01);
(Continued)

(58) Field of Classification Search
None
See application file for complete search history.

(56) References Cited

U.S. PATENT DOCUMENTS 6,764,758 B1  7/2004  Grunze et al.
8,377,243 B2  2/2013  Golzhauser et al.
(Continued)

FOREIGN PATENT DOCUMENTS

CN  102661882       9/2012
CN  102661882 A  *  9/2012

OTHER PUBLICATIONS

Water assisted higly efficient synthesis of impurity free single walled carbon nanotube, Hata et al. , Nov. 19, 2004, vol. 306, Science (Year: 2004).*

(Continued)

*Primary Examiner* — Peter A Salamon
(74) *Attorney, Agent, or Firm* — Renner, Otto, Boisselle & Sklar, LLP (57) ABSTRACT

The present invention discloses functionalized nanomembranes, a method for preparation and their use. The functionalized nanomembrane comprises a) a first layer comprising a nanomaterial, b) a second layer comprising a biorepulsive material, the second layer being attached to at least one side of the first layer, and c) affinity groups, attached to the second layer.

12 Claims, 6 Drawing Sheets (51) Int. Cl.
*B01J 20/32* (2006.01)
*B01J 20/28* (2006.01)
*H01J 37/26* (2006.01)

(52) U.S. Cl.
CPC .............. *H01J 37/20* (2013.01); *H01J 37/26* (2013.01); *H01J 2237/2007* (2013.01); *H01J 2237/2802* (2013.01)

(56) References Cited

U.S. PATENT DOCUMENTS

| | | | |
|---|---|---|---|
| 2005/0191620 A1* | 9/2005 | McDevitt | C12Q 1/6816 435/5 |
| 2010/0155620 A1 | 6/2010 | Hutchison et al. | |
| 2011/0014472 A1* | 1/2011 | Culver | B22F 1/0018 428/403 |
| 2011/0226413 A1 | 9/2011 | Zhang et al. | |
| 2012/0272868 A1* | 11/2012 | Berry | B82Y 30/00 106/286.8 |
| 2013/0040283 A1* | 2/2013 | Star | G01N 27/127 435/5 |
| 2013/0216581 A1* | 8/2013 | Fahmy | A61K 39/00 424/275.1 |
| 2013/0277573 A1 | 10/2013 | Miller et al. | |

OTHER PUBLICATIONS

A Graphene Oxide Stretavidin Complex for Biorecognition—Towards Affinity Purification, Lui et al., Adv.Funct. Mater. 2010, 20, 2857-2865. (Year: 2010).*

A Graphine oxide Stretavidin Comples for biorecognition—towards affinity purification, Liu et al., Adv.Funct, Mater. 2010,20,2857-2865 (Year: 2010).*

Single Molecule Accomodation of Streptavidin in Nanometer Scale Wells formed in DNA Nanostructures, Kuzuya et al, Nucleic Acids Symposium Series, No. 52, Sep. 8, 2008. (Year: 2008).*

Zunfeng Liu et al; "A Graphene Oxide Streptavidin Complex for Biorecognition—Towards Affinity Purification", Advanced Functional Materials, vol. 20, No. 17, Sep. 9, 2010, pp. 2857-2865.

Eunah Kang et al; "Specific Adsorption of Histidine-Tagged Proteins on Silica Surfaces Modified with Ni 2+/NTA-Derivatized Poly(ethylene glycol)". Langmuir, vol. 23, No. 11, May 1, 2007, pp. 6281-6288.

Christopher J. Benjamin et al; "Stabilized, Non-Fouling Transmission Electron Microscopy Grid Coatings for the Selective Capture of His-Tag T7 Virus and His-Tag Gro EL from Cell Lysates", Biophysical Journal, vol. 108, No. 2, Jan. 27, 2015, pp. 617a-618a.

PCT/EP2016/051923, PCT International Search Report and Written Opinion of the International Searching Authority dated May 10, 2016.

* cited by examiner

FIG. 6

FUNCTIONALIZED NANOMEMBRANE, A METHOD FOR PREPARATION THEREOF AND THEIR USE

The present application is a U.S. National Stage Application based on and claiming benefit and priority under 35 U.S.C. § 371 of International Application No. PCT/EP2016/051923, filed 29 Jan. 2016, which in turn claims benefit of and priority to European Application No. 15153106.8 filed 29 Jan. 2015, the entirety of both of which is hereby incorporated herein by reference.

TECHNICAL FIELD

The present invention relates to functionalized nanomembranes, a method for preparation thereof and their use.

BACKGROUND

Transmission electron microscopy (TEM) is a powerful method for the structural characterization of molecules and molecular aggregates, in particular for structural biology. To determine the structure of the specimens by TEM, they are deposited onto membranes which are thin enough to be transparent for electrons. TEM of negatively stained biological specimen is widely used to screen samples and to obtain preliminary information. To stabilize the biological samples against radiation damage by the electron beam, they are very often embedded in a very thin film of vitreous ice at cryogenic temperatures (cyroTEM).

Conventional amorphous carbon films, used routinely as support films for cryoTEM of vitrified specimens, are 10-15 nm thick. Thinner amorphous carbon films are mechanically unstable. To make things worse, the conductivity of amorphous carbon decreases with decreasing temperature. This is of particular importance for cryoTEM, where samples are studied at the temperature of liquid nitrogen or liquid helium, so that the thin carbon films become completely electrically insulating. Due to these poor electrical and mechanical properties, the imaging of specimens at these temperatures suffer from inelastic scattering, electrostatic charging and beam-induced movements, which severely limit the achievable resolution (R. Henderson, *Ultramicroscopy* 1992, 46, 1). Although direct electron detectors have been developed, which enable correction of beam-induced motion, the specimen remains the most critical part.

In addition, the deposition of the specimens onto regular membranes proceeds relatively non-selectively, so that the specimen has to be enriched/purified before investigation. In the case of proteins and protein complexes this is often hampered by low expression rates and difficulties to purify sufficient amounts of material for cryoTEM. If detergents have to be present for the sample preparation, as it is the case e.g. for the single particle cryoTEM of solubilized membrane proteins, the problem is exacerbated by the fact that the detergent can lead to depletion of membrane proteins from the holes of the holey carbon film due to reduced surface tension.

A few new support film materials for TEM other than amorphous carbon are already known in state of the art. Among other things, pristine graphene and graphene oxide layers have been already tested as support film material for TEM of inorganic and biological specimens (J. C. Meyer et al., *Nature* 2008, 454, 319; R. S. Pantelic et al., *J. Struct. Biol.* 2011, 174, 234; R. S. Pantelic et al., *Solid State Commun.* 2012, 152, 1375; R. S. Pantelic et al., *J. Struct. Biol.* 2010, 170, 152). While graphene oxide is hydrophilic and therefore more favorable for the preparation of aqueous biological samples than pristine graphene, it shows, however, only a very low conductivity, especially at low temperature. On the other hand, pristine graphene is extremely hydrophobic, hampering its application as support film for cryoTEM of ice-embedded biological samples as well as its chemical functionalization.

Another serious issue is unspecific binding of proteins to the support film. A very established way to suppress this unspecific binding is the formation of biorepulsive hydrogel layers consisting, e.g., of oligoethyleneglycol (OEG) units. These units can be attached to surfaces by different grafting strategies. In recent work, thin carbon nanomembranes have been functionalized with a protein-repulsive polyethyleneglycol layer (N. Meyerbröker et al., *ACS Appl. Mat. Interf.* 2013, 5, 5129).

To selectively bind a specimen onto such biorepulsive layer, selective molecular tags can be introduced. For this, typically OEG molecules bearing an amino or a carboxylic acid group have been used to further functionalize the hydrogel surfaces.

Only few attempts have been made to enable selective binding of specimens to the TEM support films by means of selective molecular tags. Recently, proteins have been bound to either lipid layers, 2D protein crystals functionalized with affinity groups, or antibodies, which in turn were physisorbed onto conventional carbon support films (D. F. Kelly et al., *J. Mol. Biol.* 2008, 382, 423; G. Sharma et al., *J. Struct. Biol.* 2013, 181, 190; B. G. Han et al., *J. Struct. Biol.* 2012, 180, 249; Y. Guimei et al., *J. Struct. Biol.* 2014, 187, 1). A disadvantage of this approach is the sensitivity of lipid layers and 2D protein crystals towards detergents, making them incompatible with structural analysis of e.g. detergent-solubilized membrane proteins.

SUMMARY

It is an object of the present invention to provide functionalized nanomembranes, which overcome drawbacks of the prior art, especially of current support films for biological TEM. In particular, functionalized nanomembranes shall be provided, which can be utilized as novel support films facilitating and accelerating the high-resolution structural analysis of biological specimens via TEM and enabling the direct and selective isolation of tagged biological molecules from raw mixtures, so that the sample can be studied by negative stain TEM or directly vitrified and studied via cryoTEM.

Further, functionalized nanomembranes shall be provided, which allow unleashing the full potential of cryoTEM, meaning that ultrathin and highly homogeneous functionalized nanomembranes shall be provided, which minimize inelastic scattering of electrons during measurements, are electrically conductive, and possess specific bio-recognition sites for selective binding of biomolecular specimens for a simplified sample preparation.

It is a further object of the present invention to provide a method for the preparation of functionalized nanomembranes.

The first object is achieved by functionalized nanomembranes, comprising
  a) a first layer comprising a nanomaterial,
  b) a second layer comprising a biorepulsive material, the second layer being attached to at least one side of the first layer, and
  c) affinity groups, attached to the second layer.

The term "biorepulsive material", as used herein, is intended to be materials or compounds which repel biomolecules, such as amino acids, lipids, carbohydrates, proteins, polysaccharides and/or nucleic acids.

Within the present application, the term "functionalized" is to be understood, as the formation of a chemical bond, such as a covalent, coordinative, hydrogen bond, ionic, or dispersive (van-der-Waals) bond, preferably a covalent bond, between the respective functional groups of nanomaterial, biorepulsive material and/or affinity groups.

By the term "affinity groups" is meant molecular residues or chemical groups, which exert selective binding to the particular specimens. These specific (bio)-recognition motives may lead to a higher affinity between the functionalized nanomembrane and the respective specimens.

Preferably, the first layer is consisting of a nanomaterial.

Also preferred is that the nanomaterial acts as mechanical support.

More preferably, the nanomaterial is a nanomembrane.

Preferably, the nanomaterial of the first layer is selected from a carbon nanomembrane, graphene, graphene oxide, a film of amorphous carbon and a nanomembrane of silicon, silicon nitride or silicon dioxide.

Within the present invention, the "carbon nanomembrane" consists of a nanolayer having a thickness of less than 100 nm, preferably less than 10 nm, and being preferably formed from organic precursors. The organic precursors preferably comprise low-molecular aromatic compounds, such as phenyl, biphenyl, terphenyl, naphthalene, anthracene, bipyridine, terpyridine, thiophene, bithienyl, terthienyl, pyrrol, and combinations thereof. The organic precursors preferably bear terminal groups, such as hydroxyl groups, amino groups or ester groups, representing the functional groups on which the functionalization of the carbon nanomembrane with a biorepulsive material may occur. Preferably, the "carbon nanomembrane" is a nanomembrane formed from self-assembled monolayers (SAMs) of the mentioned precursors by cross-linking.

Within the present application, as "nanomembranes of silicon, silicon nitride or silicon dioxide" preferably membranes are utilized which are commercially available, e.g. from SIMPore, as support materials for TEM. These kinds of membranes bear reactive Si—OH groups onto which a covalent binding of the biorepulsive material may occur.

It is preferred that the film of amorphous carbon has a thickness in the range of 3-30 nm, preferably 5-15 nm.

It is further preferred that the nanomembranes of silicon, silicon nitride and silicon oxide have a thickness in the range of 1-15 nm, preferably 4-6 nm, and more preferably have a thickness of about 5 nm.

Further, it is preferred that the carbon nanomembrane has a thickness in a range of 0.5-4 nm, more preferably 0.6-3 nm.

In a preferred embodiment, the functionalized carbon nanomembrane has a thickness in a range of 3-25 nm, more preferably of 3-10 nm.

More preferably, the functionalized nanomembrane is highly homogeneous regarding thickness and composition.

In a preferred embodiment, the functionalized nanomembrane is a free-standing nanomembrane.

Preferably, the biorepulsive material comprised in the second layer is at least partly arranged at the surface of the second layer, preferably substantially forms the outer surface of the second layer, that is, the surface towards the interface of the first layer and the second layer. Even preferred, the second layer is substantially consisting of the biorepulsive material.

Even preferred, the biorepulsive material consists of polyglycerol (PG), polyethyleneglycol (PEG), oligoethyleneglycol (OEG), peptides, proteins, oligo-carbohydrates, or (zwitter-)ionic polymers.

It is further preferred that the affinity group is one species selected from a specific recognition pair, preferably represented by chelate complexes/oligo-His, biotin/(strept)avidin, or specific DNA/RNA sense/antisense pairs.

According to the present invention, a "specific recognition pair" consists of two molecular motifs, which can distinguish and bind to each other in a competitive environment containing several molecular species. The affinity group is formed by only one species e.g. one molecular motifs of each specific recognition pair.

According to the present invention, a "chelate complex" is a very stable complex, formed of a polydentate ligand, preferably ethylenedinitrilotetraacetic acid (EDTA), N-nitrilotriacetic acid (NTA), or their derivatives and a cation, such as $Cu^{2+}$, $Ni^{2-}$, $Fe^{3+}$ and $Co^{2+}$, preferably $Ni^{2+}$.

The second object is achieved by a method for preparing the inventive functionalized nanomembranes, comprising the steps a) providing a first layer comprising a nanomaterial, b) functionalization of the first layer with a biorepulsive material for obtaining a second layer comprising the biorepulsive material, and c) functionalization of the second layer with affinity groups.

It is preferred that the functionalization in step b) is carried out by a grafting process.

It is further preferred that the functionalization in step c) is carried out by alkylation, acylation, or epoxide ring-opening chemistry.

Preferably, the first layer, consisting of the nanomaterial, is a nanomaterial supported on a TEM grid.

The third object is achieved by using the inventive functionalized nanomembrane as support film, preferably as support film in transmission electron microscopy (TEM), more preferably cryoTEM, for structural analysis of biomolecules.

More preferably, the functionalized nanomembrane is used supported on a TEM grid.

Preferably, all TEM grids known from the prior art may be used within the present invention, but more preferably pure TEM grids or TEM grids layered with holey carbon or TEM grids with holey gold are utilized.

Surprisingly, it was found that the novel and ultrathin functionalized nanomembranes can be utilized as TEM support films for the structural analysis of biomolecules and, further, solve the problems related to sample preparation for TEM known from the prior art. Among other things, the ultrathin and highly homogeneous functionalized nanomembranes minimize inelastic scattering of electrons during measurements and thereby improving data collection. The utilization of functionalized nanomembranes allows the direct isolation of tagged biomolecules from raw mixtures. Thus, the samples can be directly vitrified and studied via cryoTEM. The inventive functionalized nanomembrane distinguishes itself by the affinity groups, which enable specific binding of tagged biomolecules. Additionally, the biorepulsive intermediate layer prevents unspecific binding of unwanted components of the raw mixture to the membrane. Furthermore, the inventive nanomembranes may be used free-standing as well as supported on a TEM grid. The novel engineered support films are mechanical stable as free-standing nanomembranes and thereby stabilizing the vitrified samples.

BRIEF DESCRIPTION OF THE DRAWINGS

The invention is now further illustrated by the accompanying figures and detailed description from which further features and advantages may be taken. It is to be noted that the following explanations are presented for the purpose of illustration and description only; they are not intended to be exhaustive or to limit the invention to the precise form disclosed.

DETAILED DESCRIPTION

Figure 1:
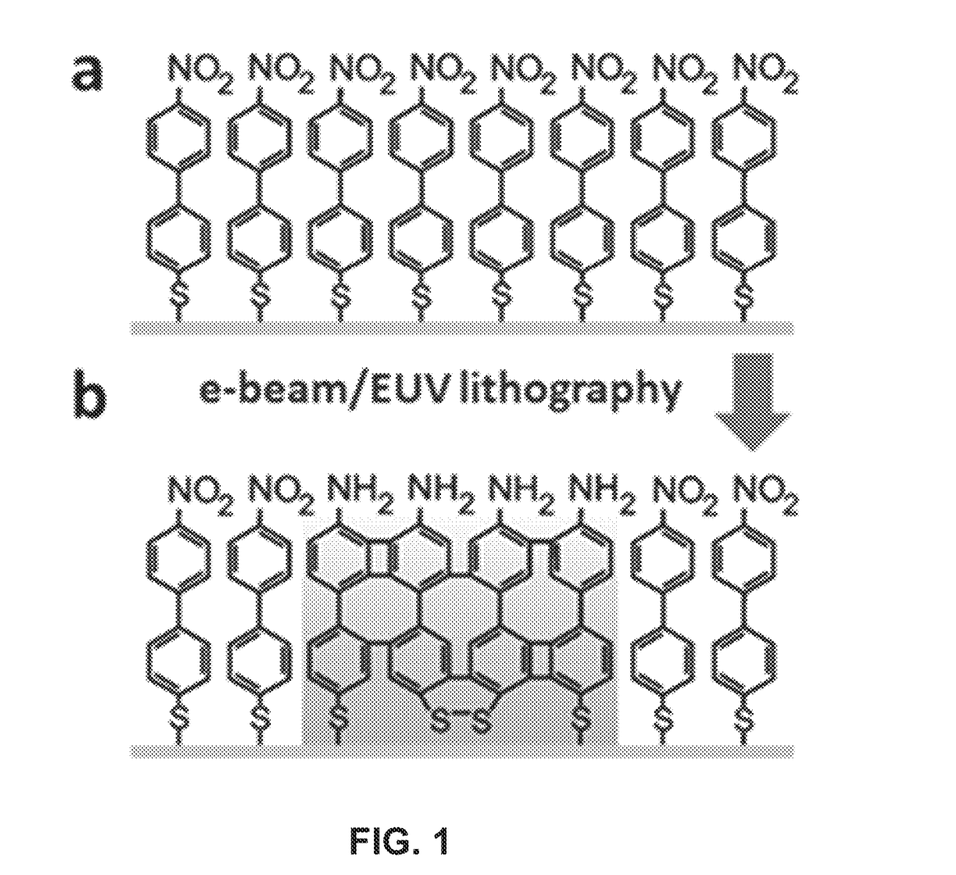
FIG. 1 schematically illustrates chemical nanolithography of a carbon nanolayer arranged on a support material.

FIG. 1 shows chemical nanolithography of a carbon nanomembrane arranged on a support material via electron irradiation or extreme UV (EUV) light. Electron irradiation of aromatic SAMs results in their lateral cross-linking (A. Turchanin et al., *Proc. Surf Sci.* 2012, 87, 108; W. Geyer et al., *Appl. Phys. Lett.* 1999, 75, 2401; A. Turchanin et al., *Langmuir* 2009, 25, 7342). The cross-linking converts the SAM into a mechanically stable molecular nanolayer with a thickness of one molecule, which can be tuned from 0.5 to 3 nm (A. Turchanin et al., *ACS Nano* 2013, 7, 6489; U.S. Pat. No. 8,377,243 B2). In case of chemical nanolithography of nitro group-terminated biphenyl SAMs, cross-linked amino-terminated areas in a 4'-nitro-1,1'-biphenyl-4-thiol (NBPT) SAM on gold may be produced. In particular, nitro groups are reduced into the respective amino groups, which may be modified for the preparation of functionalized nanomembranes (U.S. Pat. No. 6,764,758 B1).

A similar cross-linking of the aromatic SAMs can be attained with extreme UV (EUV) light. In addition, EUV opens new opportunities for the fabrication of nanopatterned nanomembranes by using EUV interference lithography (EUV-IL). EUV-IL combines the advantages of a parallel fabrication process with very high resolution below 10 nm. Its nanopatterning capability is far beyond that of photolithography, electron beam lithography, and scanning probe lithography, in terms of resolution or throughput. It may be used for making free-standing patterned nanomembranes of various shapes.

Free-standing carbon nanomembranes may also be chemically functionalized. In some cases, even a second face on the carbon nanomembrane is available for modifications. These free-standing bifacial carbon nanomembranes are usually known as "Janus nanomembranes".

Figure 2:
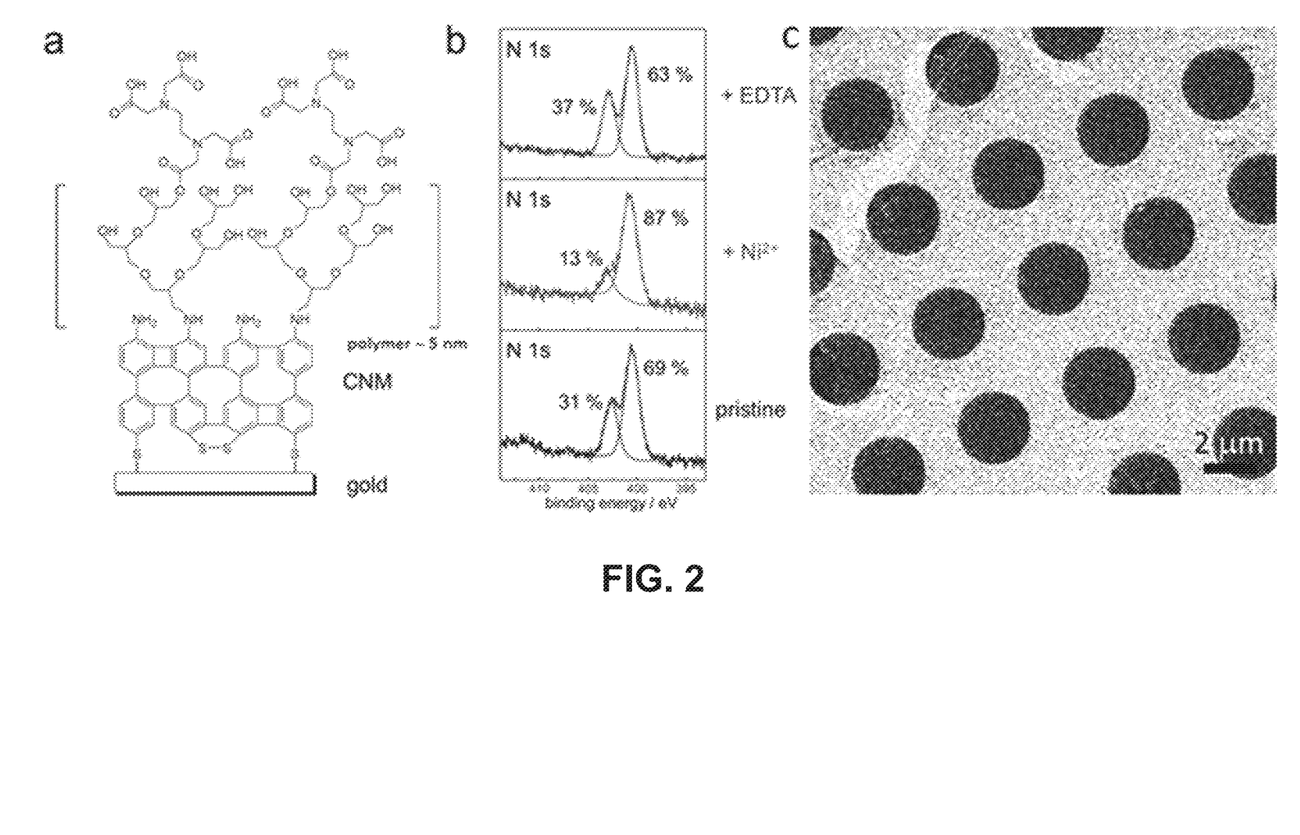
FIG. 2 shows (a) a functionalized carbon nanomembrane having PG as biorepulsive material and an EDTA derivative as affinity group, (b) a X-ray photoelectron spectra (XPS) and (c) a low-resolution helium ion microscopy (HIM) image of the free-standing functionalized carbon nanomembrane.

FIG. 2 shows a functionalized carbon nanomembrane having PG as biorepulsive material and EDTA as affinity groups. It has been shown that the amino-terminated, cross-linked surfaces could not only be rendered biorepulsive by a grafting process, but can also be modified by acylation chemistry. Preferably, multidentate ligands, such as EDTA, are used as affinity groups, which are capable of reversibly binding $Ni^{2+}$ ions. FIG. 2b shows X-ray photoelectron spectra (XPS) of a pristine functionalized carbon nanomembrane (top), the same membrane after incubation with $Ni^{2+}$ (center) and after removal of $Ni^{2+}$ with EDTA solution (bottom). XPS analysis shows that the functionalized carbon nanomembranes bind $Ni^{2+}$ reversibly, which means that a reversible attachment/detachment of the specimen becomes possible. Furthermore, free-standing PG and EDTA functionalized carbon nanomembranes were transferred from the original gold substrate onto TEM grids. FIG. 2c shows a low-resolution helium ion microscopy (HIM) image of a free-standing PG and EDTA functionalized carbon nanomembrane on a Quantifoil® TEM grid.

Figure 3:
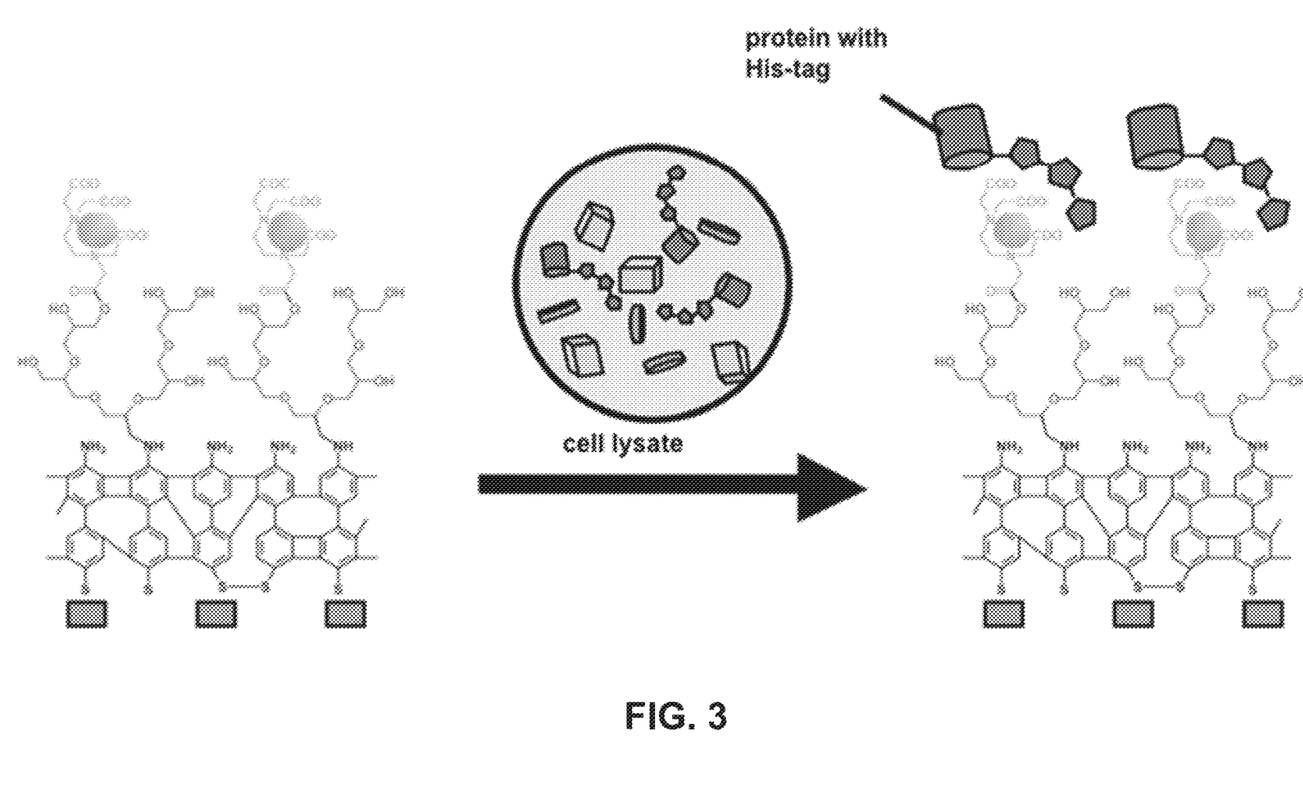
FIG. 3 shows a schematic view of using a functionalized carbon nanomembrane for in situ separation/isolation of appropriately tagged biomolecules from cell lysate.

The inventive functionalized nanomembranes may be used as TEM support films for the specific immobilization of biomolecules on their surface via bio-recognition reactions. FIG. 3 shows the concept of using the inventive carbon nanomembranes. Selective immobilization of biomolecules is achieved just by immersion of the functionalized nanomembrane into a raw mixture, for example, a cell lysate. The hydrogel intermediate layer prevents the unspecific binding of constituents of the cell lysate to the nanomembrane. The final assembly is suitable for vitrification and subsequent structural analysis by cryoTEM.

Figure 4:
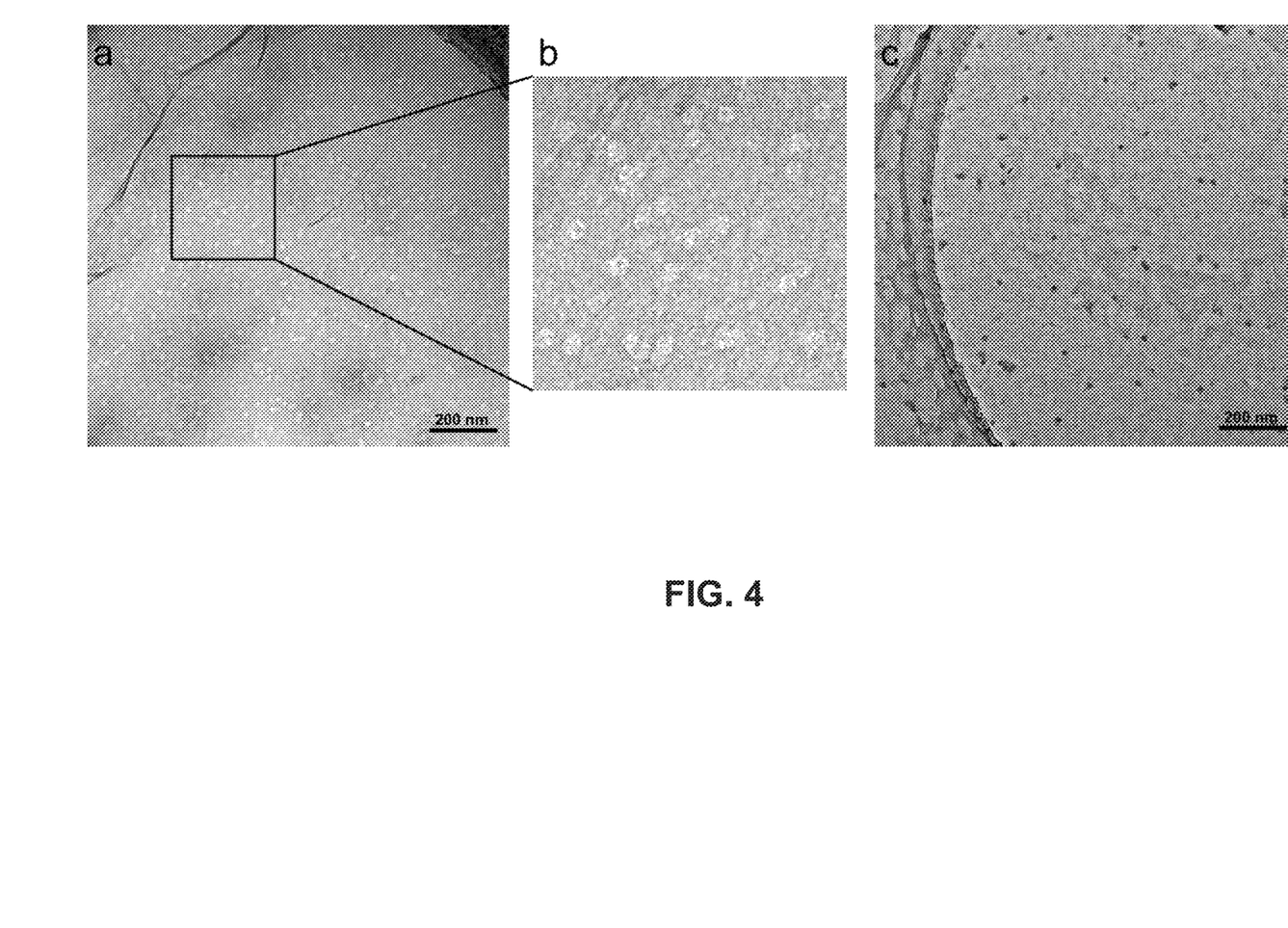
FIG. 4 shows TEM images of negatively stained polyhistidine-tagged (His-Tag) biomolecules specifically bound to PG and EDTA functionalized carbon nanomembranes.

FIG. 4 shows TEM images of negatively stained His-tagged biomolecules specifically bound to carbon nanomembranes functionalized with PG and EDTA. TEM analysis reveals that His-tagged thermosome molecules bind to functionalized carbon nanomembranes, whereas thermosomes without His-Tag do not bind to functionalized carbon nanomembranes. FIG. 4a shows a TEM image of negatively stained His-tagged thermosome molecules from *Pyrococcus furiosus* attached to the functionalized carbon nanomembrane. FIG. 4c shows a TEM image of a control experiment. It shows a functionalized carbon nanomembrane after incubation with bare thermosome without His-Tag and subsequent negative staining. Apart from dark deposits no thermosome particles are visible.

Figure 5:
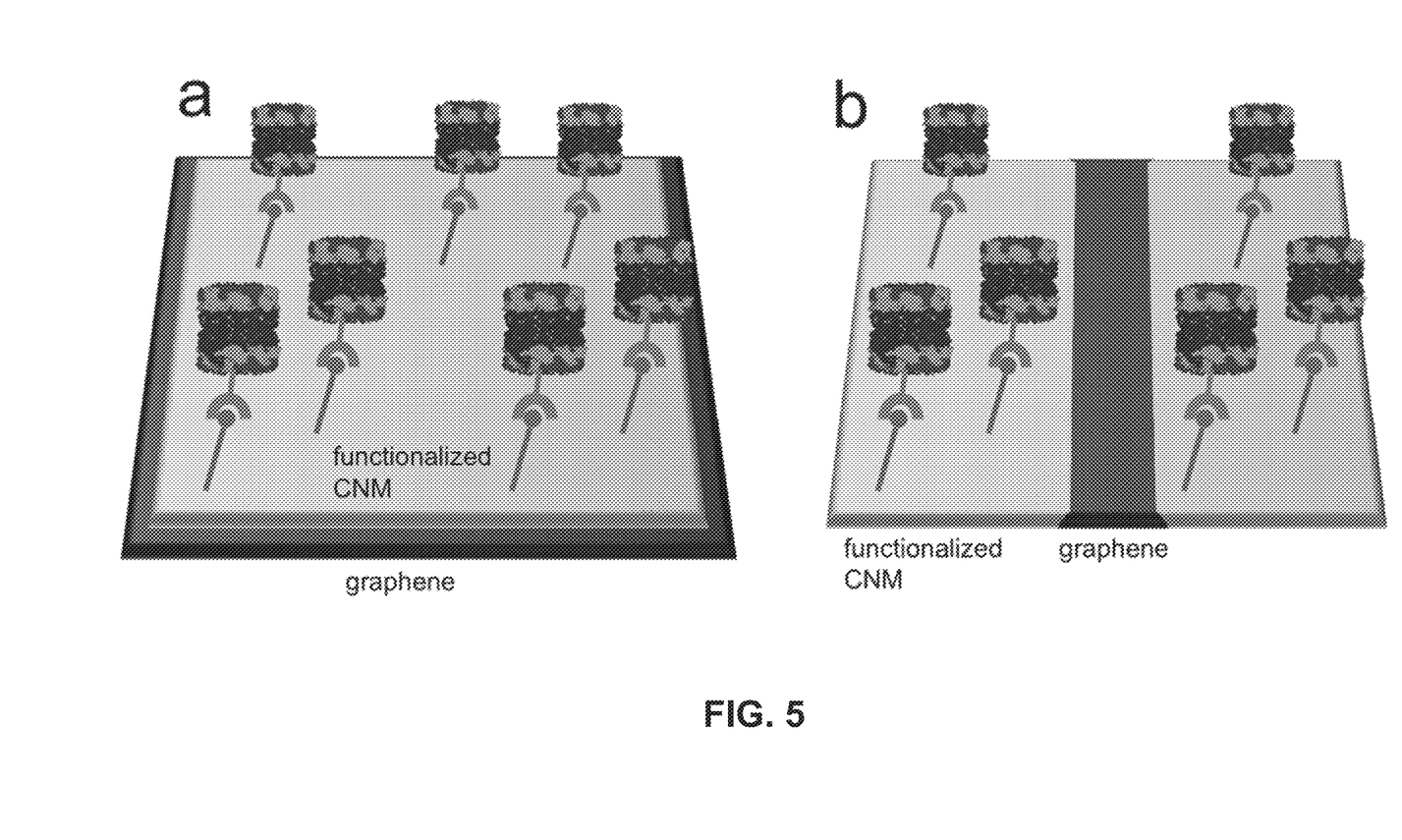
FIG. 5 shows (a) a CNM transferred to a graphene sheet and (b) functionalized CNM patterned with graphene stripes.

FIG. 5 shows how functionalized carbon nanomembranes can be coupled to graphene to enhance the conductivity to reduce sample charging during the TEM measurements. FIG. 5a shows the deposition of the functionalized nanomembrane onto a separately fabricated graphene sheet. Charges collected or formed in the nanomembrane can be easily transferred to the highly conductive graphene sheet due to the proximity (e.g. by tunneling). In FIG. 5b parts of the carbon nanomembrane have been transformed into graphene stripes, e.g. by prolonged local treatment with electrons before the remaining parts of the CNM become functionalized. During TEM analysis of biomolecules, charges are then collected by the conductive graphene stripes, which are electrically grounded. Both strategies keep the samples electrically neutral and reduce scattering effects by charge/charge interaction.

Figure 6:
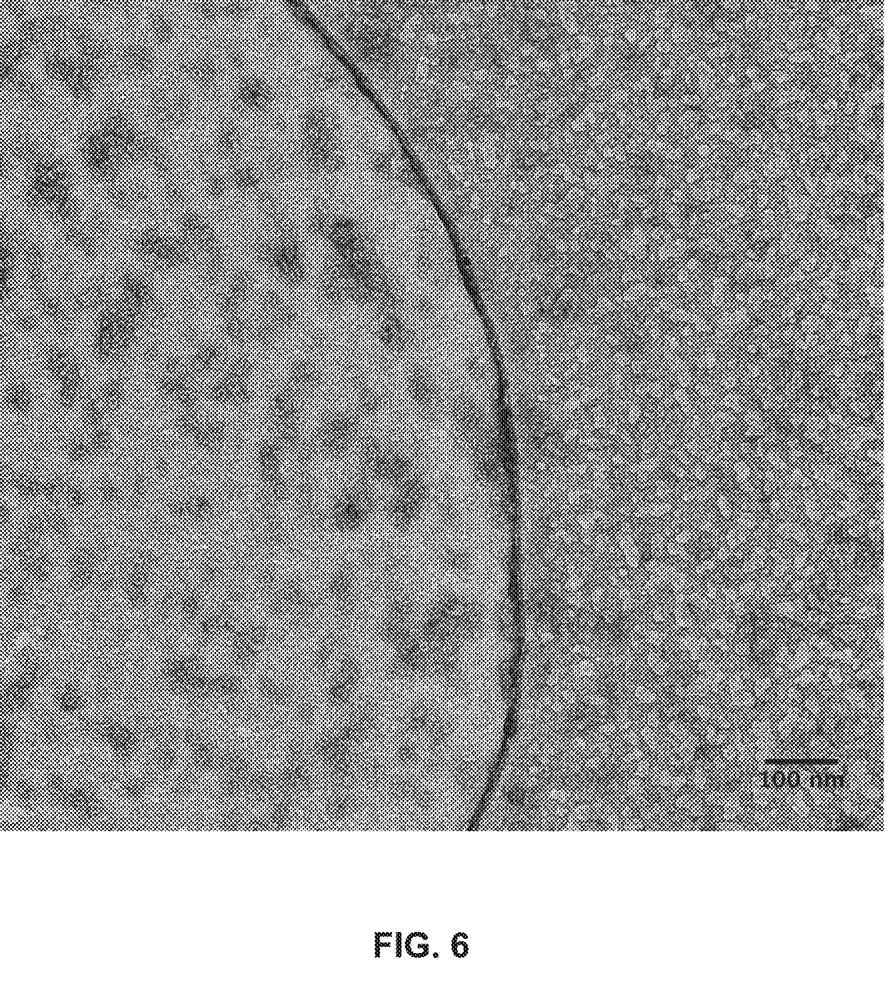
FIG. 6 shows a TEM image of negatively stained His-tagged thermosome from *P. furiosus* on functionalized amorphous carbon film mounted on Quantifoil® grids.

FIG. 6 shows a TEM image of negatively stained His-tagged thermosome from *P. furiosus* on functionalized amorphous carbon film mounted on Quantifoil® grids.

EXAMPLES

1) Formation of a Carbon Nanomembrane (CNM)

CNMs are prepared by electron irradiation induced cross-linking of 4'-nitro-1,1'-biphenyl-4-thiol (NBPT) self-assembled monolayers (SAMs) on gold. To form the SAMs, 300 nm films of thermally evaporated Au on mica are used. The substrates are cleaned in a UV/ozone-cleaner, rinsed with ethanol and blown dry in a stream of nitrogen. For the SAM formation, two methods can be used. Either the substrates are immersed in a ~10 mmol solution of NBPT in dry, degassed dimethylformamide (DMF) for 72 h in a sealed flask under nitrogen. Afterwards samples are rinsed with DMF and ethanol and blown dry with nitrogen. Alternatively, NBPT is evaporated from a Knudsen cell onto the Au films at vacua better than $10^{-5}$ mbar. Crosslinking to the CNM and conversion of the nitro groups to amino groups is achieved in high vacuum ($<5*10^{-7}$ mbar) with an electron floodgun at an electron energy of 100 eV and a dose of 50 mC/cm$^2$.

2) Formation of the Second Layer (Here: Polyglycerol)

The CNM on its gold-on-mica substrate is deposited into dry and clean polytetrafluoroethylene (PTFE) containers filled with a 10% (w/w) solution of glycidol in dry N-methylpyrrolidinone (NMP). After closing the PTFE vessels tightly, it is heated in an oven to 150° C. for 10 h. After cooling, the films are taken out, washed with NMP, water, and acetone, and then dried in the ambient under exclusion of dust.

3) Functionalization of the Second Layer with Affinity Groups (Here: EDTA)

The disodium salt of ethylenediaminetetraacetic acid ($Na_2EDTA \times 2\ H_2O$, 510 mg) was dispersed in dry dimethylformamide (DMF, 15 mL) and thionylchloride (0.3 mL) was added. After stirring at room temperature for 2 h, the mixture was heated to 80° C. for 45 min. After cooling, the film system was immersed immediately in this reaction mixture and shaken at 50 rpm for 2 h. Then the films were taken out and purged with DMF, ethanol, water, and acetone. Drying took place in the ambient under exclusion of dust.

4) Lifting the Film Systems Off and Transfer to the TEM Grids

The functionalized CNMs are transferred onto TEM grids using a protecting layer of poly(methyl methacrylate) (PMMA) dissolved in chlorobenzene or ethyl acetate. This layer is used for mechanical stabilization of the CNMs during the transfer process. Two layers of this polymer of overall thickness of ~400 nm are spin-coated in sequence onto the CNM. First, a layer of low molecular weight PMMA (50 K), then a layer of high molecular weight PMMA (950 K) are spin-cast each for 30 s at 4000 rpm and cured on a hot plate at 90° C. for 5 min. The underlying mica support is separated from the gold/functionalized CNM/PMMA structure by a slight dipping into water of one of the edges/corners of the multilayered sample that finally (after separation) floats on the air/water interface. Further, the sample is transferred by using a mica piece from the water surface to an $I_2/KI/H_2O$ etching bath (1:4:10) where the gold film is dissolved within 15 min. Then the CNM is transferred to pure water for complete cleaning of the membrane from iodine contamination. Finally, the CNM/PMMA structure is fished out by the target substrate, a TEM grid, and the PMMA layer is dissolved in acetone using a critical point dryer to minimize damage of the freestanding parts.

5) Electron Microscopy of Biological Samples on Functionalized CNM (Here: Based on EDTA/Ni$^{2+}$/His-tag Interaction)

The functionalized CNM on a TEM grid was incubated with 3 μl NiCl$_2$ (1 mg/mL Ni$^{2+}$ in PBS buffer) for 30 seconds and rinsed with distilled water. Subsequently, 3 μl of protein solution (His-tagged thermosome from *Pyrococcus furiosus*, ~0.2 mg/ml) were applied to the functionalized CNM for 30 seconds, rinsed with distilled water and negatively stained with 1% uranylacetate solution. Samples were analyzed in a FEI Tecnai Spirit transmission electron microscope at an accelerating voltage of 120 kV. Images were acquired with a 4 k×4 k CCD camera (Gatan).

6) Functionalization of Amorphous Carbon Film

Continuous amorphous carbon films on gold-on-mica substrate are treated with oxygen plasma. Films having a defined thickness ranging from 2 to 10 nm were utilized. A thickness of 4 to 5 nm was found to exhibit advantageous balance between mechanical stability and transparency. Analogously to the functionalization of CNMs, the plasma treated amorphous carbon film on its gold-on-mica substrate is deposited into dry and clean PTFE containers filled with a 10% (w/w) solution of glycidol in dry NMP. After closing the PTFE vessels tightly, it is heated in an oven to 140° C. for 6-24 h. After cooling, the films are taken out, immersed for 10 min in water, and then dried in a stream of nitrogen. By way of example, the second layer was functionalized with EDTA groups by heating the substrate in a 0.1% (w/w) solution of EDTA monoanhydride in absolute DMF to 90° C. for 1 h. By varying the EDTA monoanhydride concentration, the functional group loading of the surface can be varied. The functionalized amorphous carbon films are transferred to TEM grids following the protocol (see example 4). By way of example, films were transferred to Quantifoil® holey carbon coated TEM grids. Transfer to holey gold or holey/lacey carbon coated or pure TEM grids can be achieved analogously. The functionalized amorphous carbon films can be coupled to graphene (as shown for CNMs in FIG. 5) to enhance the conductivity to reduce sample charging during the TEM measurements.

7) Electron Microscopy of Biological Samples on Functionalized Amorphous Carbon Film (Here: Based on EDTA/Ni$^{2+}$/His-tag interaction)

To activate the functionalized amorphous carbon film, 3 μl 1 mM NaOH were added, blotted, and washed once with distilled water. Subsequently, 3 μl 0.1% NiSO4 solution were added and left for 30 s. The sample was washed twice with 3 μl distilled water. 3 μl of sample was added to the grid and left for 30 s. The grid was blotted with filter paper. The grid was washed twice with 3 μl distilled water, blotted, and stained with Uranyl acetate. Samples were analyzed in an FEI Tecnai Spirit at an acceleration voltage of 120 kV.

The features disclosed in the foregoing description, claims and the drawings may, both separately or in any combination, be material for realizing the invention in diverse forms thereof.

The invention claimed is:

1. Functionalized nanomembrane, comprising
   a) a first layer consisting of a nanomaterial, selected from a carbon nanomembrane and a film of amorphous carbon,
   b) a second layer comprising a biorepulsive material, the second layer being attached to at least one side of the first layer, and
   c) affinity groups, attached to the second layer,
   wherein one or more chemical bonds between respective functional groups of the nanomaterial, the biorepulsive material, and the affinity groups are comprised in a functionalized nanomembrane,
   wherein the biorepulsive material substantially forms an outer surface of the second layer, wherein said outer surface of the second layer forms an interface between the first layer and the second layer and the second layer substantially consists of the biorepulsive material;
   wherein the carbon nanomembrane has a thickness in a range of 0.5-4 nm; and
   wherein when the functionalized nanomembrane is a functionalized carbon nanomembrane, the functionalized carbon nanomembrane has a thickness in a range of 3-25 nm.

2. Functionalized nanomembrane according to claim 1, wherein the biorepulsive material consists of polyglycerol (PG), polyethyleneglycol (PEG), oligoethyleneglycol (OEG), peptides, proteins, oligo-carbohydrates, or (zwitter-) ionic polymers.

3. Functionalized nanomembrane according to claim 1, wherein the affinity group is one species selected from a specific recognition pair.

4. Method for preparing a functionalized nanomembrane according to claim 1, comprising the steps
   a) providing a first layer comprising a nanomaterial,
   b) functionalization of the first layer with a biorepulsive material for obtaining a second layer comprising the biorepulsive material, and
   c) functionalization of the second layer with affinity groups.

5. Method according to claim 4, wherein the first layer, consisting of the nanomaterial, is a nanomaterial supported on a TEM grid.

6. A method of structural analysis of biomolecules, comprising using the functionalized nanomembrane, according to claim 1, as support film in transmission electron microscopy (TEM).

7. The method of structural analysis, comprising using the functionalized nanomembrane according to claim 6, wherein the functionalized nanomembrane is supported on a TEM grid.

8. Functionalized nanomembrane according to claim 1, wherein the functionalized carbon nanomembrane has a thickness in a range of 3-10 nm.

9. Functionalized nanomembrane according to claim 1, wherein the biorepulsive material consists of polyglycerol (PG), polyethyleneglycol (PEG), oligoethyleneglycol (OEG), peptides, proteins, oligo-carbohydrates, or (zwitter-) ionic polymers.

10. Functionalized nanomembrane according to claim 1, wherein the affinity group is one species selected from a specific recognition pair.

11. Functionalized nanomembrane according to claim 1, wherein the affinity group is one species selected from a specific recognition pair comprising chelate complexes/oligo-His, biotin/(strept)avidin, or specific DNA/RNA sense/antisense pairs.

12. Functionalized nanomembrane according to claim 10, wherein the specific recognition pair comprises chelate complexes/oligo-His, biotin/(strept)avidin, or specific DNA/RNA sense/antisense pairs.

* * * * *